(12) United States Patent
Inoue

(10) Patent No.: US 11,147,450 B2
(45) Date of Patent: Oct. 19, 2021

(54) OPHTHALMIC IMAGING APPARATUSES AND METHOD FOR THE SAME

(71) Applicant: CANON KABUSHIKI KAISHA, Tokyo (JP)

(72) Inventor: Hiroyuki Inoue, Kawasaki (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 68 days.

(21) Appl. No.: 16/582,841

(22) Filed: Sep. 25, 2019

(65) Prior Publication Data

US 2020/0015677 A1  Jan. 16, 2020

Related U.S. Application Data

(63) Continuation of application No. PCT/JP2018/010886, filed on Mar. 19, 2018.

(30) Foreign Application Priority Data

Mar. 27, 2017 (JP) .............................. JP2017-061534

(51) Int. Cl.
*A61B 3/15* (2006.01)
*A61B 3/12* (2006.01)

(52) U.S. Cl.
CPC ............ *A61B 3/154* (2013.01); *A61B 3/1225* (2013.01)

(58) Field of Classification Search
CPC ........... A61B 3/14; A61B 3/0025; A61B 3/12; A61B 3/102; A61B 3/0058; A61B 3/1225;

(Continued)

(56) References Cited

U.S. PATENT DOCUMENTS

2006/0215112 A1* 9/2006 Nishio .................. A61B 3/103
351/205
2008/0231808 A1* 9/2008 Van de Velde ...... A61B 3/1025
351/221

(Continued)

FOREIGN PATENT DOCUMENTS

JP          2-84931 A     3/1990
JP       2016-28674 A     3/2016

(Continued)

OTHER PUBLICATIONS

Yusufu N. Sulai, et al. ;"Visualization of Retinal Vascular Structure and Perfusion with a Nonconfocal Adaptive Optics Scanning Light Ophthalmoscope;" J. Opt. Soc. Am. A, vol. 31, No. 3, pp. 569-579.

*Primary Examiner* — William R Alexander
*Assistant Examiner* — Sharrief I Broome
(74) *Attorney, Agent, or Firm* — Canon U.S.A., Inc. IP Division

(57) ABSTRACT

An ophthalmic imaging apparatus includes a first splitting unit configured to split return light from a subject irradiated with measurement light in two directions, first and second light receiving units configured to receive the first and second light beams obtained by the first splitting unit through first and second apertures disposed in respective optical paths of the first and second light beams, respectively, a generation unit configured to generate an image in accordance with light reception signals from the first and second light receiving units; and a moving unit configured to move the first and second apertures in a plane perpendicular to an optical axis. The moving unit moves the first and second apertures independently.

14 Claims, 10 Drawing Sheets

(58) Field of Classification Search
CPC ..... A61B 3/0008; A61B 3/113; A61B 3/1025; A61B 3/145; A61B 3/0041; A61B 3/0091; A61B 3/103; A61B 3/1005; A61B 3/1015; A61B 3/117; A61B 3/112; A61B 3/107; A61B 3/13; A61B 3/0033; G01B 9/02091; G01B 9/02044; G01B 9/02004; G01B 9/02027; G01B 2290/45; G01B 2290/70; G01B 9/0203; G01B 9/02083; G01B 2290/65; G01B 9/02041; G01B 9/02087; G01B 11/2518; G01B 9/0201; G01B 9/02011; G01B 9/02028; G01B 9/02034; G01B 9/02039; G01B 9/02045; G01B 9/02048; G01B 9/0205; G06T 2207/30041; G06T 2207/10101; G06T 7/0012; G06T 2207/20056; G06T 2207/30104; G06T 5/50; G06T 7/0016; G06T 7/248; G06T 7/337; G06T 15/00; G06T 15/04; G06T 2207/10028; G06T 2207/10048; G06T 2207/10144; G06T 2207/20081; G06T 2207/30096; G06T 2207/30101; G06T 3/0018; G06T 3/0062; G06T 3/4053; G02B 27/141; G02B 26/101; G02B 27/0068; G02B 2027/0187; G02B 26/0833; G02B 27/1013; G02B 7/023; G02B 7/04; G02B 13/0095; G02B 17/006; G02B 17/08; G02B 17/0832; G02B 2027/0118; G02B 2027/0127; G02B 2027/0138; G02B 2027/014; G02B 2027/0178; G02B 2027/0185; G02B 21/0012; G02B 21/0048; A61F 9/007; A61F 2009/00851; A61F 2009/00897; A61F 9/00736; A61F 9/008; A61F 9/00821; A61F 2009/00863; A61F 2009/0087; A61F 2009/00887; A61F 2250/0002; A61F 2/1624; A61F 9/00814; A61F 9/00823; A61F 9/00825; A61F 9/0084; A61F 9/009; A61F 9/013

See application file for complete search history.

(56) References Cited

U.S. PATENT DOCUMENTS

| | | | |
|---|---|---|---|
| 2016/0235294 A1* | 8/2016 | Utagawa | A61B 3/0025 |
| 2017/0055831 A1* | 3/2017 | Miwa | A61B 3/1015 |
| 2017/0196450 A1* | 7/2017 | Sato | A61B 5/0068 |

FOREIGN PATENT DOCUMENTS

| | | |
|---|---|---|
| JP | 2016-150090 A | 8/2016 |
| JP | 2017-12580 A | 1/2017 |
| JP | 2017-42308 A | 3/2017 |

* cited by examiner

OPHTHALMIC IMAGING APPARATUSES AND METHOD FOR THE SAME

CROSS-REFERENCE TO RELATED APPLICATIONS

This application is a Continuation of International Patent Application No. PCT/JP2018/010886, filed Mar. 19, 2018, which claims the benefit of Japanese Patent Application No. 2017-061534, filed Mar. 27, 2017, both of which are hereby incorporated by reference herein in their entirety.

TECHNICAL FIELD

The present invention relates to ophthalmic imaging apparatuses and a method for the same, and in particular, to an ophthalmic imaging apparatus for capturing a fundus image for use in ophthalmologic examination or the like.

BACKGROUND ART

Eye examination using an ophthalmic imaging apparatus is widely performed for the purpose of early treatment of lifestyle-related diseases and diseases that are main causes of blindness. An example of the ophthalmic imaging apparatus is a scanning laser ophthalmoscope (SLO) which is an ophthalmic imaging apparatus using the principle of a confocal laser microscope. The SLO is an apparatus that scans the fundus with a laser beam serving as measurement light to capture a high resolution planar image at high speed from the intensity of its return light.

Such an SLO can capture a shallow depth of focus, high-contrast subject eye image by selectively receiving reflected light (confocal light) from a measurement light converging point of the subject eye. Furthermore, a technique for imaging a microscopic living organism by selectively receiving diffused light (nonconfocal light) from the vicinity of a measurement light converging point has been established.

Another imaging apparatus including a plurality of light receiving elements that selectively receive diffused light is provided. This imaging apparatus is capable of capturing an image in which the edge of a microscopic, directional living organism (for example, blood vessels, blood vessel walls, and nerve fiber layers) is enhanced by changing the positions of light reception and computing light reception signals therefrom. This provides useful images for diagnosis.

PTL 1 provides a member including apertures for confocal light and apertures for nonconfocal light at a plurality of positions to change the region of the received diffused light with a simple configuration. PTL 1 discloses a technique for imaging by receiving diffused light by switching a plurality of apertures to change the region that receives the diffused light depending on the orientation of the subject living organism in the image.

PTL 2 discloses a technique for generating an enhanced image suitable of diagnosis by increasing the number of light receiving elements that receive diffused light and performing computational processing according to the orientation of the living organism in imaging after receiving the diffused light.

CITATION LIST

Patent Literature

PTL 1 Japanese Patent Laid-Open No. 2017-12580
PTL 2 Japanese Patent Laid-Open No. 2016-28674

However, the apparatus disclosed in PTL 1 cannot receive each light of a plurality of regions of the diffused light at the same time. Therefore, this apparatus has room for improvement for motion artifacts, such as involuntary eye movement and pulsing motion, which are issues in imaging using ophthalmic imaging apparatuses.

The apparatus disclosed in PTL 2 needs at least three light receiving elements to capture an enhanced image for a desired orientation, so that it has room for simplifying the apparatus configuration.

SUMMARY OF INVENTION

The present invention provides an apparatus configured to capture an enhanced image in a desired orientation and coping with motion artifacts.

An ophthalmic imaging apparatus in an aspect of the present invention includes a first splitting unit configured to split return light from a subject irradiated with measurement light into first and second light beams, first and second light receiving units configured to receive the first and second light beams obtained by the first splitting unit through first and second apertures disposed in respective optical paths of the first and second light beams, respectively, a generation unit configured to generate an image in accordance with light reception signals from the first and second light receiving units; and a moving unit configured to move the first and second apertures in a plane perpendicular to an optical axis. The moving unit moves the first and second apertures independently.

Further features of the present invention will become apparent from the following description of exemplary embodiments with reference to the attached drawings.

DESCRIPTION OF EMBODIMENTS

Embodiments of the present invention will be described in detail hereinbelow. It is to be understood that the following embodiments are not intended to limit the present invention according to the claims and that not all combinations of the features described in the embodiments are essential for the solution of the present invention.

First Embodiment

A first embodiment of the present invention will be described hereinbelow with reference to the attached drawings.

In the present embodiment, an adaptive optics (AO) SLO apparatus to which the present invention is applied will be described as the ophthalmic imaging apparatus. The AOSLO apparatus includes an adaptive optical system to capture a high-resolution planar image (an AOSLO image) of the fundus. The AOSLO apparatus includes the following units to help capturing the AOSLO image. That is, a wide field (WF) SLO unit for capturing a wide field planar image (a WFSLO image) of the fundus, an anterior eye observation unit for capturing an image of the anterior part of the subject eye to perform alignment with the subject eye and ascertain the measurement light incident position, and a fixation light display unit that guides the line of sight to adjust the image capture position.

The present embodiment provides an AOSLO apparatus that corrects a wavefront aberration generated due to the subject eye, which is a test object, using a spatial light modulator to capture a planar image, which provides a good planar image of the fundus regardless of the visibility of the subject eye and the optical aberration due to the subject eye.

Although the present embodiment includes an adaptive optical system for capturing a high-resolution planar image, any other optical system that achieves high resolution without the adaptive optical system may used.

Configuration of AOSLO Apparatus

Figure 1A:
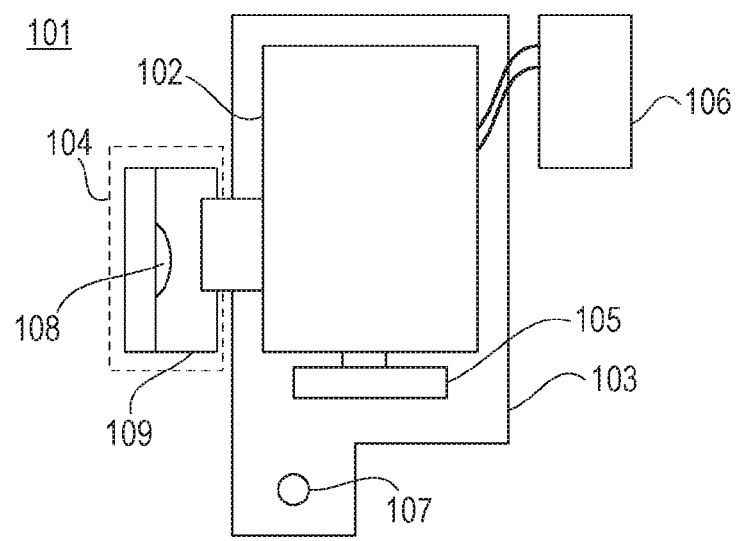
FIG. 1A is a top view of an ophthalmic imaging apparatus according to a first embodiment of the present invention.
Figure 1B:
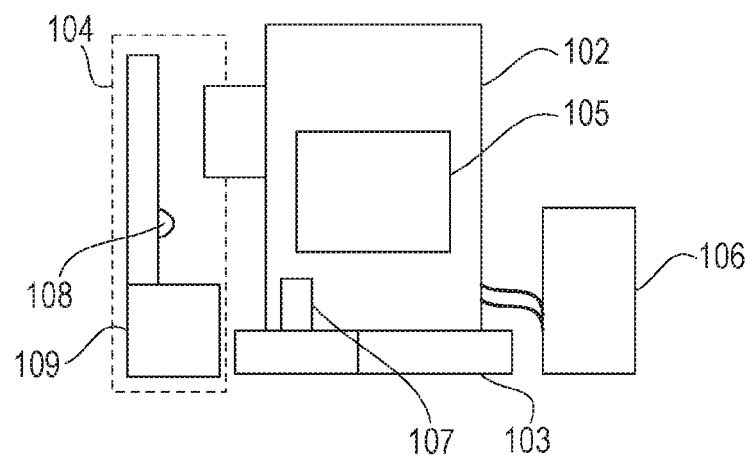
FIG. 1B is a side view of the ophthalmic imaging apparatus according to the first embodiment.

Referring to FIGS. 1A and 1B, the configuration of an AOSLO apparatus 101 in the present embodiment will be described.

FIG. 1A is a top view of the AOSLO apparatus 101, and FIG. 1B is a side view of the AOSLO apparatus 101. The AOSLO apparatus 101 includes a head unit 102 having optical systems therein, a stage 103 for moving the head unit 102 in the horizontal and vertical directions, a face holder 104 on which the face of the subject is to be placed for positioning, a liquid crystal monitor 105 that displays an operating screen or the like, and a control PC 106 that controls the entire AOSLO apparatus 101.

The head unit 102 disposed on the stage 103 is movable in the horizontal direction (the direction parallel to the plane of FIG. 1A) by tilting a joystick 107 and in the vertical direction (the direction perpendicular to the plane of FIG. 1A) by rotating the joystick 107. The face holder 104 includes a chin holder 108 on which the chin of the subject is to be placed and a chin holder driving unit 109 for moving the chin holder 108 using an electrically driven stage.

Configuration of Control Unit

Figure 2:
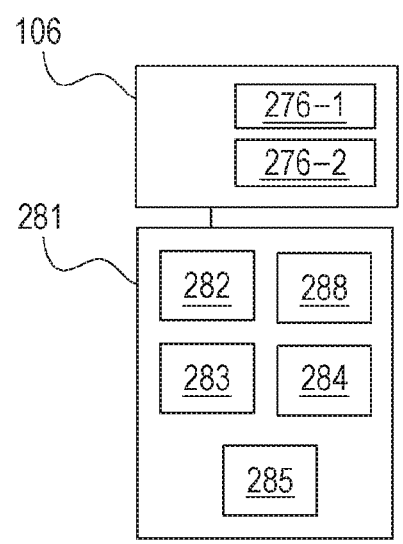
FIG. 2 is a block diagram of a control unit according to the first embodiment.

Referring next to FIG. 2, the configuration of a control unit for the AOSLO apparatus 101 in the present embodiment will be described.

The control PC 106 controls the entire AOSLO apparatus 101. The control PC 106 includes an analog-to-digital (AD) board 276-1 that converts voltage signals obtained by detectors 704-1 to 704-3 (described below) to digital values and an AD board 276-2 that converts a voltage signal obtained by a detector 238-2 (described below) to a digital value.

A driver unit 281 is connected to the control PC 106. The driver unit 281 includes an optical-scanner driver 282, an electrically-driven-stage driver 283, a fixation light driver 284, an electrically-driven-stage driver 285, and a spatial-light-modulator driver 288. The details of the operations will be described below.

Configuration of Optical System

Figure 3:
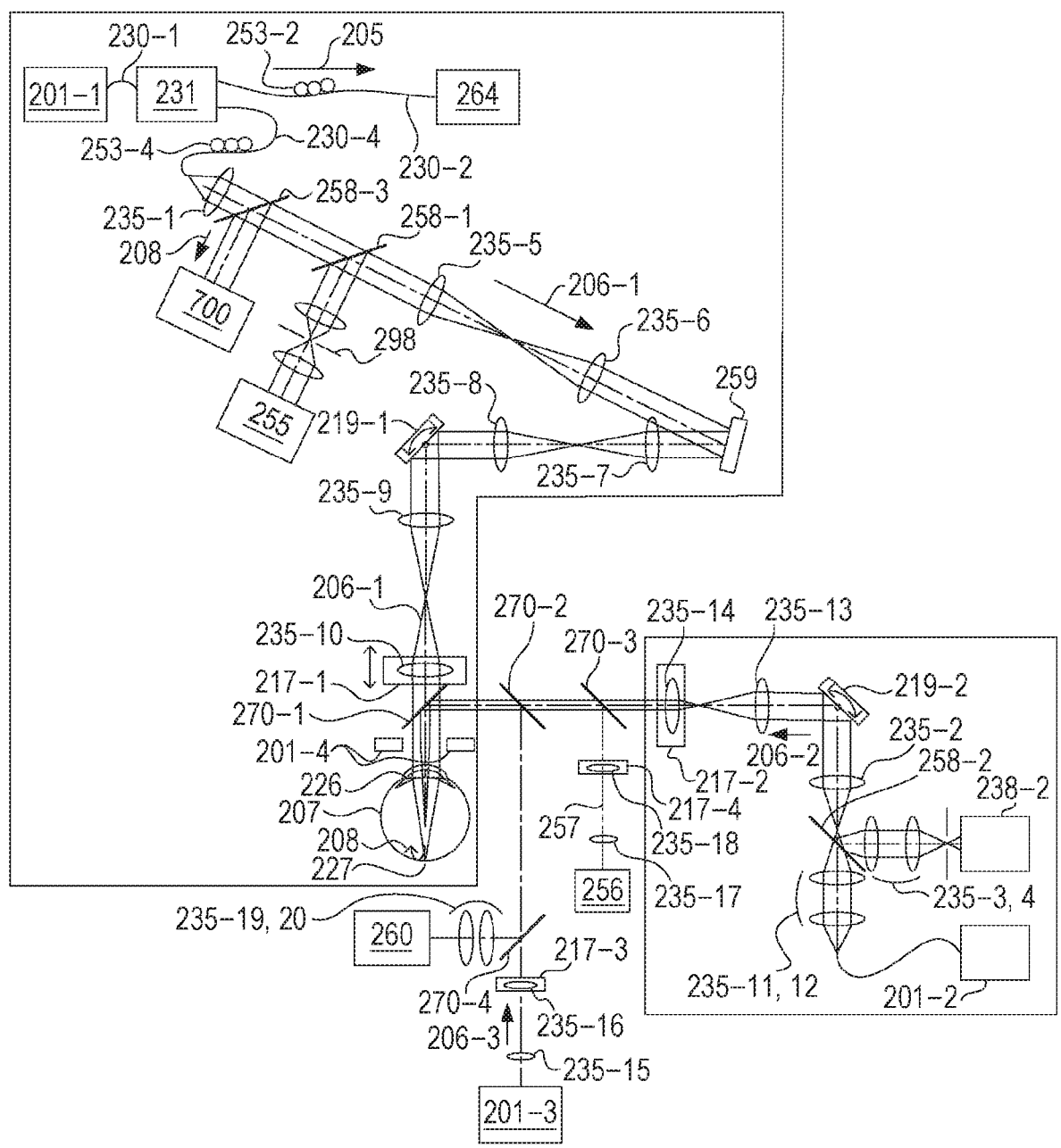
FIG. 3 is a block diagram of an optical system according to the first embodiment.

Referring to FIG. 3, the configurations of an AOSLO optical system, a beacon optical system, a WFSLO optical system, a fixation light optical system, and an anterior-eye observation optical system built in the head unit 102 will be described.

Configuration of AOSLO Optical System

Light emitted from a light source 201-1 of the AOSLO optical system enters an optical coupler 231 through a single mode fiber 230-1 and is split into reference light 205 and measurement light 206-1. Reference signs 253-2 and 253-4 denote polarization controllers.

The light source 201-1 is a super luminescent diode (SLD) light source, which is a typical low-coherent light source. The light source 201-1 has a wavelength of 840 nm and a bandwidth of 50 nm. The low coherent light source is used to capture a planar image with low speckle noise. The kind of light source is not limited to the SLD light source, and any other light source that emits low coherent light, such as an amplified spontaneous emission (ASE) light source, may be used. For the wavelength, near-infrared light is suitable to measure the eyes. Furthermore, it is desirable that the wavelength be as short as possible because the wavelength influences the resolution of the captured planar image in the lateral direction, and here, it is set at 840 nm. Another wavelength may be selected depending on the measurement site to be observed.

The reference light 205 obtained by splitting the light with the optical coupler 231 enters a light-quantity measuring apparatus 264 through an optical fiber 230-2. The light-quantity measuring apparatus 264 measures the light quantity of the reference light 205 to monitor the light quantity of the measurement light 206-1.

Next, a measurement light path of the measurement light 206-1 will be described. The measurement light 206-1 obtained by splitting the light with the optical coupler 231 is guided to a lens 235-1 through a single mode fiber 230-4, where the measurement light 206-1 is adjusted to substantially parallel light having a beam diameter of 4 mm. The measurement light 206-1 adjusted to substantially parallel light passes through beam splitters 258-3 and 258-1 and lenses 235-5 and 235-6 and enters a spatial light modulator 259. The spatial light modulator 259 is controlled by the control PC 106 via the spatial-light-modulator driver 288 in the driver unit 281.

Although a reflection spatial light modulator is used as an aberration correction device, a transmission spatial light modulator or a deformable mirror (DM) may be used.

The measurement light 206-1 is modulated by the spatial light modulator 259, passes through lenses 235-7 to 235-8, and enters the mirror of an X-Y scanner 219-1. Although the X-Y scanner 219-1 in the drawing includes one mirror for simplification, the X-Y scanner 219-1 actually includes two mirrors of an X scanner and a Y scanner disposed close to each other to raster scan over a retina 227 with the measurement light 206-1 in the direction perpendicular to the optical axis. The mirrors of the X-Y scanner 219-1 are adjusted so that the center of the measurement light 206-1 is aligned with the rotation center of each mirror of the X-Y scanner 219-1. The X scanner is a scanner that scans the measurement light 206-1 in the direction parallel to the plane of the drawing. The X scanner is a resonant scanner. The Y scanner is a scanner that scans the measurement light 206-1 in the direction perpendicular to the plane of the drawing. The Y scanner is a galvanometer scanner. The drive waveform of the galvanometer scanner is a saw-tooth waveform. The X-Y scanner 219-1 is controlled by the control PC 106 via the optical-scanner driver 282 in the driver unit 281. Lenses 235-9 and 235-10 constitute an optical system for scanning the retina 227 with the measurement light 206-1 and function to scan the retina 227 with the measurement light 206-1, with the center of the pupil of the subject eye 207 as the fulcrum.

Although the beam diameter of the measurement light 206-1 is 4 mm here, the beam diameter may be increased to capture a higher-resolution optical image. An electrically driven stage 217-1 is movable in the directions indicated by the arrows to move the position of an accompanying lens 235-10 to thereby adjust the focal position. The electrically driven stage 217-1 is controlled by the control PC 106 via the electrically-driven-stage driver 283 in the driver unit 281. Adjusting the position of the lens 235-10 allows the measurement light 206-1 to focus onto a predetermined layer of the retina 227 of the subject eye 207 to observe the retina 227 and capture an image thereof. This also applies to a case in which the subject eye 207 has a refractive error.

When the measurement light 206-1 enters the subject eye 207, the light is reflected or diffused by the retina 227 into return light 208, which travels backward through the measurement light path and is reflected by the beam splitter 258-3 into a light receiving unit 700. The details of the configuration of the light receiving unit 700 will be described below. The incident return light 208 is split and extracted by splitting units and apertures into the detectors 704-1 to 704-3 (see FIG. 4). The intensity of the return light 208 is converted to a voltage signal, and the voltage signal is output for use in generating a planar image of the fundus of the subject eye 207. Examples of the detectors 704-1 to 704-3 include an avalanche photo diode (APD) and a photomultiplier tube (PMT), which are high-speed, highly sensitive optical sensors.

Although the present embodiment uses a refracting optical system in which the entire AOSLO optical system mainly uses lenses, a reflecting optical system using spherical mirrors instead of the lenses may be used.

Configuration of AOSLO Light-Receiving Optical System

Figure 4:
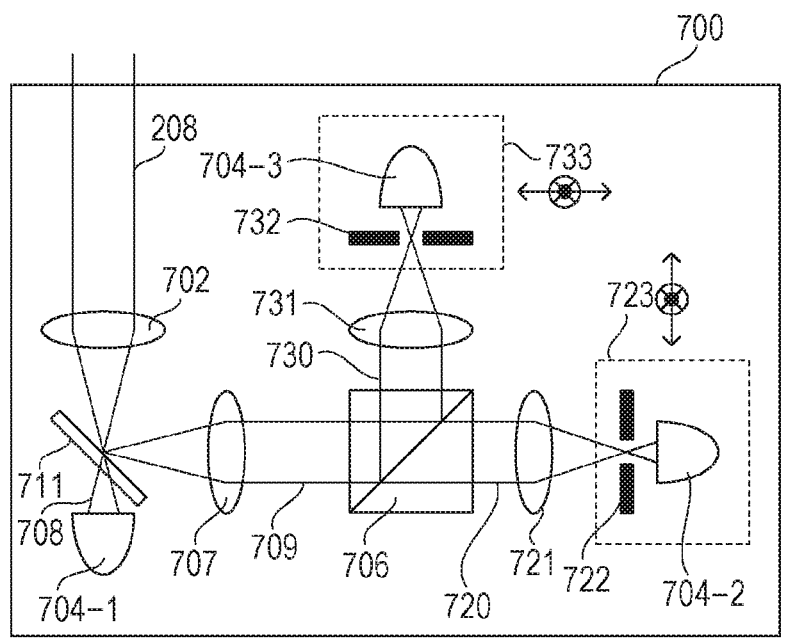
FIG. 4 is a block diagram of a light receiving unit according to the first embodiment.
Figure 5:
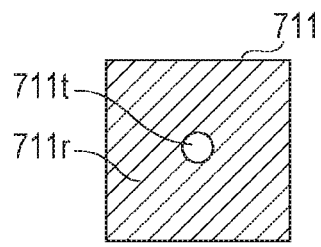
FIG. 5 is a diagram illustrating a splitting unit according to the first embodiment.
Figure 6:
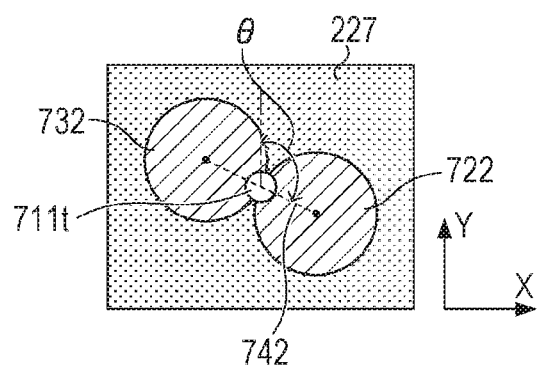
FIG. 6 is a diagram illustrating apertures according to the first embodiment.

Referring next to FIGS. 4 to 6, the light receiving unit 700 will be described.

In FIG. 4, the return light 208 incident on the light receiving unit 700 is focused on a splitting unit 711 disposed at a position conjugate to the fundus by a lens 702 and is split into a confocal light 708 and nonconfocal light 709. The details of the splitting to the confocal light 708 and the nonconfocal light 709 using the splitting unit 711 will be described below.

The confocal light 708 enters the detector 704-1, where the light 708 is converted to a voltage signal according to the intensity of the light, and the voltage signal is transmitted to the control PC 106. The voltage signal is converted to a digital value by the AD board 276-1 in the control PC 106. In the control PC 106, data processing synchronizing with the operation and the drive frequency of the X-Y scanner 219-1 is performed to generate an AOSLO image (a confocal image).

The nonconfocal light 709 enters a lens 707. The nonconfocal light 709 is collimated to substantially parallel light by the lens 707 and enters a splitting unit 706, such as a beam splitter cube, where the light is split by amplitude into transmitted light 720 and reflected light 730 at a ratio of 50:50. The transmitted light 720 is converged by a lens 721 onto a light shielding member (hereinafter simply referred to as "aperture") 722 having an aperture (opening) disposed at a position conjugate to the fundus, and the light passing through the aperture 722 enters a detector 704-2. The aperture 722 and the detector 704-2 are connected to an electrically driven stage 723 and are moved in a plane perpendicular to the optical axis of the transmitted light 720, with their positional relationship kept.

The reflected light 730 is converted by the lens 731 onto an aperture 732 disposed at a position conjugate to the fundus, and the light passing through the aperture 732 enters the detector 704-3. The aperture 732 and the detector 704-3 are connected to an electrically driven stage 733 and is moved in a plane perpendicular to the optical axis of the reflected light 730, with their positional relationship kept. The electrically driven stages 723 and 733 are controlled by the control PC 106 via the electrically-driven-stage driver 285 in the driver unit 281.

The light incident on the detectors 704-2 and 704-3 is converted to voltage signals according to the intensity of the light. The voltage signals are transmitted to the control PC 106, where voltage signals are converted to digital values by the AD board 276-1 in the control PC 106. In the control PC 106, data processing synchronizing with the operation and the drive frequency of the X-Y scanner 219-1 is performed to generate an AOSLO image (a nonconfocal image). The AOSLO image is processed (described later) into an edge enhanced image whose edge is enhanced.

Referring to FIGS. 4 and 5, the splitting unit 711 will be described. FIG. 5 is a diagram of the splitting unit 711 viewed from the optical axis of the incident return light 208. The splitting unit 711 is a pinhole mirror and has a transmission region 711t at the center, through which only light confocal to spot light of the measurement light 206-1 converged on the retina 227 is transmitted. Only the confocal light 708 passing through the central transmission region 711t enters the detector 704-1.

The transmission region 711t is formed in elliptical shape viewed in the direction perpendicular to the reflection surface so as to be circular in shape as viewed in the optical axis of the return light 208 when the splitting unit 711 is disposed at an angle relative to the optical axis of the return light 208. The diameter of the transmission region 711t viewed from the direction of the optical axis of the return light 208 depends on the spot diameter that is achieved when the measurement light 206-1 is converged onto the retina 227 and the magnification of the AOSLO optical system, which is about 68 µm in the present embodiment. A region of the splitting unit 711 around the central transmission region 711t is a reflecting region 711r. Such a configuration can be achieved by evaporating reflection coating onto glass or opening a hole in part of a mirror. This configuration allows the confocal light 708, which is transmitted light guided to the detector 704-1, to be limited to confocal light converged onto the retina 227, providing high-contrast AOSLO image with a shallow depth of focus. The nonconfocal light 709, which is reflected light from the peripheral reflecting region 711r, mainly contains a diffused light component having information on the microstructure of the subject, and is suitable for imaging a microstructure. Furthermore, since the optical axis direction of the nonconfocal light 709 can be freely changed depending on the angle of disposition of the splitting unit 711, the flexibility of the layout of the optical system can be increased with a simpler configuration, so that a more compact apparatus can be provided. The relationship between the transmission and the reflection of the splitting unit 711 is not limited to the above. The confocal region may be a reflected region, and the nonconfocal region may be a transmission region. This has the advantage of making ghost light hardly enter the confocal region.

Referring next to FIG. 6, the layout of the apertures 722 and 732 will be described.

FIG. 6 is a conceptual diagram illustrating an image in which the transmission region 711*t* of the splitting unit 711, which is disposed at a position conjugate to the fundus, and the apertures 722 and 732 (the inside of each hatched circle is a transmission region, or an opening), which are disposed at positions conjugate to the fundus, are virtually disposed on the fundus retina 227 of the subject eye. Here, θ denotes an angle formed by a straight line 742 connecting the aperture 722 and the aperture 732 and the Y-axis (a direction perpendicular to the optical axis and the plane of the drawing, and the X-axis is a direction perpendicular to the optical axis and parallel to the plane of the drawing on the retina 227 in FIG. 3). The angle θ is set by the operator or the control PC 106 in an aperture angle setting operation described below. When θ is set, the electrically driven stage 723 is driven by the electrically-driven-stage driver 285 in response to a control signal from the control PC 106 to move the aperture 722 and the detector 704-2 to the position in the X-Y plane illustrated in FIG. 6. The electrically driven stage 733 is driven by the electrically-driven-stage driver 285 in response to a control signal from the control PC 106 to move the aperture 732 and the detector 704-3 in the X-Y plane to the position illustrated in FIG. 6. In FIG. 6, the aperture 722 and the aperture 732 are disposed so as to be symmetrical about a converging point (the center of the transmission region 711*t*).

With such an aperture configuration, the value I23 of each pixel of the edge enhanced image is expressed as Eq. (1).

$$I23=(I2-I3)/(I2+I3) \quad (1)$$

Here, I2 is the digital value of the light-receiving signal of light passing through the aperture 722 received by the detector 704-2 at a certain point in time. I3 is the digital value of light passing through the aperture 722 received by the detector 704-3 at the same point in times as I2.

This calculation allows comparing the intensities of diffused light at spatially different positions, thereby enhancing a structure whose degrees of diffusion differ depending on the orientation to provide an edge enhanced image. In particular, for a structure having directivity perpendicular to the straight line 742 connecting the apertures 722 and 732, this calculation allows capturing an edge enhanced image.

With this configuration, since the transmission region 711*t* where a largest amount of return light is transmitted is used to guide the light to the detector 704-1 for use in generating a confocal image, a high-contrast, high-resolution confocal image can be captured, and at the same time, an edge enhanced image can be captured. Furthermore, since confocal light does not enter the photodetectors 704-2 and 704-3, a small difference in diffused light intensity can also be extracted.

In the present embodiment, although the aperture 722 and the detector 704-2, and the aperture 732 and the detector 704-3 are individually moved together, only the aperture 722 and the aperture 732 may be moved. This requires increasing the light-receiving areas of the detectors 704-2 and 704-3 to allow the light passing through the aperture 722 and the aperture 732 to enter the detectors 704-2 and 704-3, respectively, even if the aperture 722 and the aperture 732 are moved.

Configuration of Beacon Optical System

Referring to FIG. 3, the beacon unit for measuring aberration that occurs at the subject eye 207 will be described.

Measurement light 206-3 emitted from a light source 201-3 is applied to the subject eye 207, which is an observation target, through lenses 235-15 and 235-16, a dichroic mirror 270-4, and so on.

The measurement light 206-3 is incident off the center of the cornea 226 of the subject eye 207 to avoid reflection from the cornea 226. Part of return light 208″ of the measurement light 201-3 enters a wavefront sensor 255 through the beam splitter 258-1, such as a dichroic mirror, and a pinhole 298, and the wavefront aberration of the return light 208 that occurs at the subject eye 207 is measured. The pinhole 298 is disposed to block unnecessary light other than the return light 208″. The wavefront sensor 255 is electrically connected to the control PC 106. The wavefront sensor 255 is a Shack-Hartmann wavefront sensor. The aberration information obtained by the wavefront sensor 255 is expressed by the control PC 106 using Zernike polynomials. The center wavelength of the light source 201-3 is 760 nm, and the wavelength width is 20 nm.

The lenses 235-5 to 235-10 and so on are disposes so that the cornea 226, the X-Y scanner 219-1, the wavefront sensor 255, and the spatial light modulator 259 have an optically conjugate positional relationship. This allows the wavefront sensor 255 to measure the wavefront aberration due to the subject eye 207. This also allows the spatial light modulator 259 to correct the wavefront aberration due to the subject eye 207.

Although the present embodiment illustrates a configuration for measuring the wavefront aberration due to the subject eye 207 using beacon light, this is not intended to limit the present invention. For example, the measurement light 206-1 may also serve as wavefront measurement light. In this case, the return light 208 of the measurement light 206-1 reflected and diffused from the retina 227 travels back through the measurement light path and is reflected by the beam splitter 258-1 into the wavefront sensor 255, so that the wavefront aberration due to the subject eye 207 is measured.

Configuration of WFSLO Optical System

Next, the WFSLO optical system will be described with reference to FIG. 3. The WFSLO optical system can capture a planar image of the subject eye with a wider angle of view than the AOSLO optical system and is useful in determining an AOSLO image capturing position. The WFSLO optical system has substantially the same configuration as the configuration of the AOSLO optical system. For this reason, descriptions of like parts will be omitted.

The measurement light path of WFSLO measurement light 206-2 will be described. The measurement light 206-2 emitted from a light source 201-2 is applied to the subject eye 207 to be observed via lenses 235-11 and 235-12, a beam splitter 258-2, a lens 235-2, an X-Y scanner 219-2, lenses 235-13 and 235-14, and dichroic mirrors 270-3, 270-2, and 270-1.

The light source 201-2 is an SLD light source as in the AOSLO unit and has a wavelength of 920 nm and a bandwidth of 20 nm.

An X scanner, which is a component of the X-Y scanner 219-2, is a resonant scanner that scans the measurement light 206-2 in the direction parallel to the plane of the drawing. A Y scanner is a galvanometer scanner that scans the measurement light 206-2 in the direction perpendicular to the plane of the drawing. Its drive waveform is a saw-tooth waveform.

Although the beam diameter of the measurement light 206-2 is 1 mm here, the beam diameter may be increased to capture a higher-resolution image.

When the measurement light 206-2 is incident on the subject eye 207, the measurement light 206-2 is reflected and diffused from the retina 227 to become return light 208'. The return light 208' travels back through the measurement light path, is deflected in a reflection direction by the beam splitter 258-2, and enters the detector 238-2 via the lenses 235-3 and 235-4.

The light applied to the detector 238-2 is converted to a voltage signal according to the intensity of the light. The voltage signal detected by the detector 238-2 is transmitted to the control PC 106 and is converted to a digital value by the AD board 276-2 in the control PC 106. The digital value is processed in synchronism with the operation and the drive frequency of the X-Y scanner 219-2 by the control PC 106 to generate a WFSLO image.

Configuration of Fixation Light Optical System

Next, the fixation light optical system will be described. The fixation light optical system is an optical system for projecting fixation light with a predetermined shape onto a predetermined position of the subject eye to prompt the subject to fix the eye.

A fixation light 256 is a light-emitting display module. Examples include a liquid crystal display, an organic electroluminescent (EL) display, and a light-emitting diode (LED) array including a display surface on an X-Y plane. A beam 257 from the fixation light 256 is applied to the retina 227 via lenses 235-17 and 235-18 and the dichroic mirrors 270-1 to 270-3. The lenses 235-17 and 235-18 are disposed so that the display surface of the fixation light 256 and the retina 227 have an optically conjugate positional relationship. The fixation light 256 is controlled by the control PC 106 via the fixation light driver 284 in the driver unit 281.

By the subject eye 207 gazing at the beam 257 projected from the fixation light 256, the subject eye 207 is prompted to fix or rotate. The display surface of the fixation light 256 displays, at any position, for example, a lighting or blinking cross, rectangular, or circular pattern.

Configuration of Anterior-Eye Observation Optical System

Next, the anterior-eye observation optical system will be described. An anterior eye image of the subject eye captured by the anterior-eye observation optical system is useful in aligning the subject eye with the apparatus.

Light emitted from an anterior-eye lighting light sources 201-4 is applied to the subject eye 207, and its reflected light enters a charge-coupled device (CCD) camera 260 via dichroic mirrors 270-1, 270-2, and 270-4 and lenses 235-19 and 235-20. The light sources 201-4 are LEDs with a center wavelength of 740 nm.

Focus, Shutter, and Astigmatism Correction

As described above, the optical system built in the head unit 102 includes the AOSLO unit, the beacon unit, the WFSLO unit, the fixation light unit, and the anterior-eye observation unit. Among them, the AOSLO unit, the beacon unit, the WFSLO unit, and the fixation light unit include the electrically driven stages 217-1 to 217-4, respectively, and adjust the focal position by cooperatively moving the four electrically driven stages 217-1 to 217-4. However, the focal position can also be individually adjusted by moving the electrically driven stages 217-1 to 217-4 individually. The AOSLO unit, the WFSLO unit, and the beacon unit each include a shutter (not illustrated). By opening and closing the shutter, application of the measurement light to the subject eye 207 can be controlled individually. Although shutters are used here, the application of the measurement light can be controlled by turning on and off the light sources 201-1 to 201-3. Likewise, the anterior-eye observation unit and the fixation light unit can also be controlled by turning on and off each light source 201-4 and the fixation light 256, respectively.

The lens 235-10 is interchangeable, so that a spherical lens or a cylindrical lens can be used in accordance with aberration (refractive error) due to the subject eye 207. Not only one lens but also a combination of a plurality of lenses may be installed.

Control Software Screen

Figure 7:
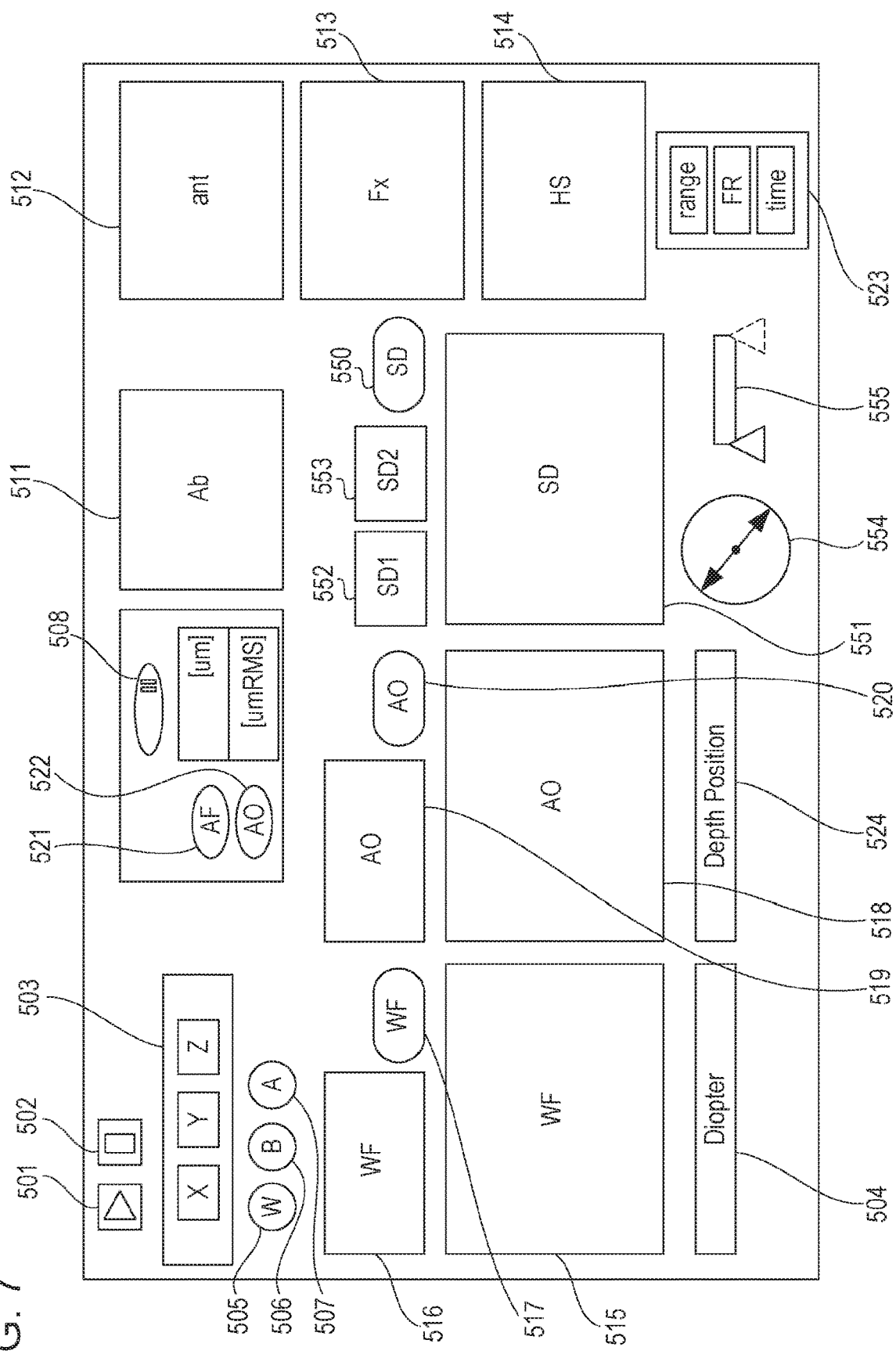
FIG. 7 is a diagram illustrating a control software screen according to the first embodiment.

Next, a control software screen displayed on the liquid crystal monitor 105 will be described with reference to FIG. 7. In FIG. 7, the individual reference signs are as follows.

Reference sign 501 denotes an execution button for use in giving an instruction to start image capturing. 502 denotes a STOP button for use in giving an instruction to end the processing. 503 denotes an electrically driven stage button for use in giving an instruction to accurately adjust the chin holder 108. 504 denotes a focus adjustment button for use in adjusting focusing. 505 denotes a WFSLO-image capturing button for use in giving an instruction to start capturing a WFSLO image. 506 denotes an aberration measurement button for use in giving an instruction to start measurement of aberration. 507 denotes an AOSLO-image capturing button for use in giving an instruction to start capturing an AOSLO image. 508 denotes an aberration-correction pause button for use in giving an instruction to temporarily stop correction of aberration. 511 denotes an aberration-correction display unit for use in displaying the value of aberration. 512 denotes an anterior-eye display unit for use in displaying an anterior eye image. 513 denotes a fixation-light-position display unit for use in giving an instruction for a position where the fixation light 256 is to be lit. 514 denotes a wavefront-sensor display unit for use in displaying a Hartmann image detected by the wavefront sensor 255. 515 denotes a WFSLO display unit for use in displaying a WFSLO image. 516 denotes a WFSLO intensity display unit for use in displaying the intensity of a signal output from the detector 238-2. 517 denotes an WFSLO record button for use in giving an instruction to record a WFSLO image. 518 denotes an AOSLO display unit for use in displaying an AOSLO (confocal) image. 519 denotes an AOSLO intensity display unit for use in displaying the intensity of a signal output from the detector 704-1. 520 denotes an AOSLO record button for use in giving an instruction to record an AOSLO image. 521 denotes an auto-focus button for use in giving an instruction to perform auto-focusing. 522 denotes an aberration correction button for use in giving an instruction to start aberration correction. 523 denotes a capturing-condition setting button for use in giving an instruction to change set capturing conditions. 524 denotes a depth adjustment button for use in giving an instruction to adjust the depth of an AOSLO image to be captured. 550 denotes an edge enhancement mode button for use in giving an instruction to set a nonconfocal-image edge enhancement mode.

Reference sign 551 denotes an edge-enhanced-image display unit for use in displaying edge-enhanced-images captured by the detector 704-2 and the detector 704-3. 552 denotes a nonconfocal-image display unit for use in displaying a nonconfocal image captured by the detector 704-2. 553 denotes a nonconfocal-image display unit for use in displaying a nonconfocal image captured by the detector 704-3. 554 denotes an angle adjustment unit for use in changing the angle for edge enhancement. 555 denotes an aperture-interval adjustment unit for use in adjusting the interval between the aperture 722 and the aperture 732. The details of the operations will be described in a second embodiment.

Processing Procedure of Image Capturing

The processing procedure of image capturing performed by the AOSLO apparatus of the present embodiment will be described with reference to FIGS. 8 and 9.

Figure 8:
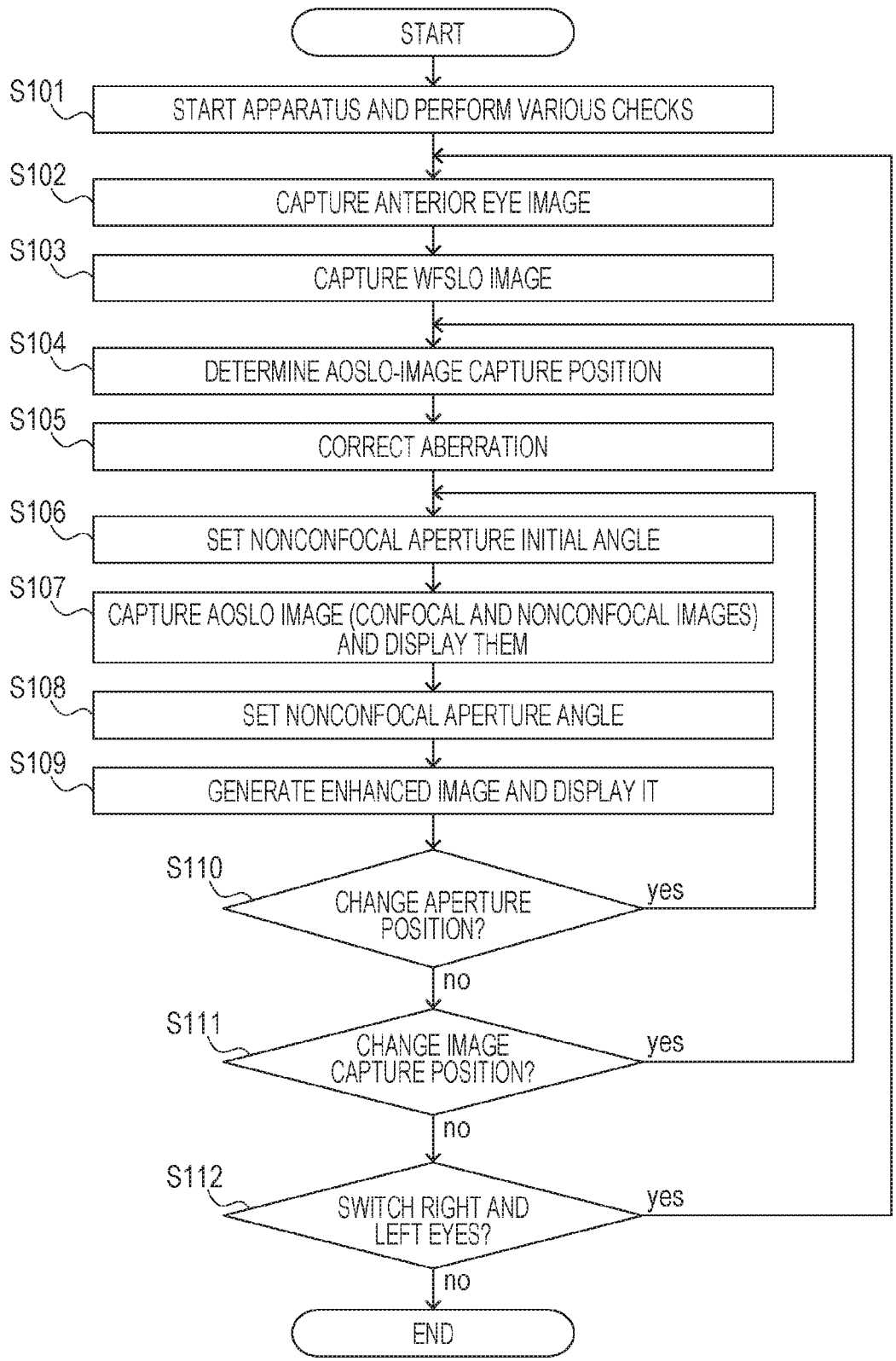
FIG. 8 is a flowchart for capturing processing according to the first embodiment.

FIG. 8 illustrates the processing procedure of image capturing in the present embodiment. The individual processes will be described below. The processes are controlled by the control PC 106 unless otherwise specified.

First, at step S101, the AOSLO apparatus is started, and various checks are performed.

When an operator turns on the power of the control PC 106 and the AOSLO apparatus, measurement control software is started in the apparatus to display the control software screen illustrated in FIG. 7 on the liquid crystal monitor 105. In this state, the operator asks the subject to place the face on the face holder 104.

Next, at step S102, an anterior eye image is captured.

When the execution button 501 on the control software screen is pressed by the operator, the anterior-eye display unit 512 displays an image of the anterior eye captured by the CCD camera 260. If the center of the pupil is not displayed in a substantially correct state at the center of the anterior-eye display unit 512, the operator moves the head unit 102 to the substantially correct position using the joystick 107. If further adjustment is required, the operator presses the electrically driven stage button 503 on the control software screen to move the chin holder driving unit 109 finely.

Next at step S103, a WFSLO image is captured. If an anterior eye image is displayed in a substantially correct state, a WFSLO image captured by the detector 238-2 is displayed on the WFSLO display unit 515. The fixation light is set to the center with the fixation-light-position display unit 513 to lead the line of sight of the subject eye 207 to the center. Next, the operator gives an instruction to adjust focusing using the focus adjustment button 504 while viewing the WFSLO intensity display unit 516. The operator gives an instruction to adjust focusing so that the signal intensity displayed on the WFSLO intensity display unit 516 is increased. The WFSLO intensity display unit 516 displays signal intensity detected by the detector 238-2 of the WFSLO unit in chronological order, with time on the horizontal axis, and signal intensity on the vertical axis. Since the instruction using the focus adjustment button 504 is given, the positions of the lenses 235-10, 235-14, 235-16, and 235-18 are moves at the same time to adjust the focal position. In response to the operator confirming that a WFSLO image is clearly displayed on the WFSLO display unit 515 and pressing the WFSLO record button 517, WFSLO data is stored in a storage unit (not illustrated).

Next, at step S104, a position at which an AOSLO image is to be captured is determined.

The operator checks the WFSLO image displayed on the WFSLO display unit 515 to determine a desired AOSLO image capture position using the means described later. The operator leads the line of sight of the subject eye 207 using the fixation light 256 so that the capture position comes to the center of the WFSLO display unit 515. There are two means for determining the position to capture the AOSLO image. One is a method in which the operator designates the position of fixation light on the fixation-light-position display unit 513 and turns on the fixation light at the designated position. The other is a method in which the operator designates a desired position on the WFSLO display unit 515. The pixels on the WFSLO display unit 515 and the position of the fixation light are stored in association with each other. The position of the fixation light is automatically moved according to the instruction to lead the line of sight to a desired position. When the operator confirms that the desired AOSLO image capture position has moved to the center of the WFSLO display unit 515, the process proceeds to the next step.

Next at step S105, aberration correction is performed.

When the operator presses the aberration measurement button 506, the measurement light 206-2, which is WFSLO measurement light, is blocked, the shutter for beacon light emitted from the light source 201-3 is opened to apply the measurement light 206-3, which is beacon light, to the subject eye 207. A Hartmann image detected by the wavefront sensor 255 is displayed on the wavefront-sensor display unit 514. Wavefront aberration calculated from the Hartmann image is displayed on the aberration-correction display unit 511. The wavefront aberration is displayed in parts, a defocus component (in μm) and the amount of all aberrations (in μmRMS). Since at step S103 the positions of the lenses 235-10 and 235-16, which are respective focus lenses for the AOSLO measurement light and the beacon light, are adjusted, it is ready for aberration measurement at this step. Specifically, this allows the return light 208" of the measurement light 206-3 to pass through the pinhole 298 without being blocked to reach the wavefront sensor 255. When the auto-focus button 521 is pressed here, the positions of the lenses 235-10, 235-14, 235-16, and 235-18 are adjusted so that the values of defocusing are decreased. When the operator presses the aberration correction button 522, the spatial light modulator 259 is adjusted in a direction in which the amount of aberration decreases, and the amount of aberration is displayed in real time. When the amount of aberration reaches a predetermined threshold (for example, 0.03 μmRMS) or less, the AOSLO-image capturing button 507 is automatically pressed, and the process proceeds to the next step. The threshold of the amount of aberration can be freely set. If the amount of aberration does not reach the threshold or less, the operator presses the aberration-correction pause button 508 to stop the aberration correction and then presses the AOSLO-image capturing button 507, thereby proceeding to the next step.

Next at step S106, the initial angles of the nonconfocal apertures are set.

Here, the initial angle of θ, which is the angle that a straight line connecting the nonconfocal apertures 722 and 732 forms with the Y-axis, is set before an AOSLO image is captured at the next step S107. This initial angle, which is stored in a memory (not illustrated) built in the control PC 106, is preferably an angle that is easy for the operator to recognize, such as an angle parallel to the X-direction or the Y-direction. However, this is merely an example. The initial angle may be an angle at the previous examination.

Directions in which blood vessels and ganglion fiber layers in a human eye fundus run have some tenancy for each region, although there are individual differences. For this reason, the running direction of a structure that automatically comes into the angle of view when the AOSLO image capture position is determined at step S104 may be estimated by the control PC 106, and then the angles of the nonconfocal apertures may be determined in a direction perpendicular to the running direction. Thus, by automatically estimating the angles of the nonconfocal apertures and disposing the nonconfocal apertures at these angles, the man-hours of the operator can be reduced, and the throughput can be increased.

Next at step S107, an AOSLO image is captured.

When the operator presses the AOSLO-image capturing button 507, the measurement light 206-3, which is beacon light, is blocked, and the shutter of the AOSLO measurement light 206-1 is opened to apply the measurement light 206-1 to the subject eye 207. Thus, an AOSLO image whose aberration is corrected is displayed on the AOSLO display unit 518. Furthermore, the nonconfocal-image display units 552 and 553 display nonconfocal images captured by the detectors 704-2 and 704-3, respectively.

Like the WFSLO intensity display unit 516, the AOSLO intensity display unit 519 displays signal intensity detected by the detector 704-1 of the AOSLO unit in a chronological order. If the signal intensity is insufficient, the operator gives an instruction to adjust the focal position and the position of the chin holder 108 while viewing the AOSLO intensity display unit 519 so that the signal intensity increases. The operator also designates the angle of image capturing, a frame rate, and an image capturing period using the capturing-condition setting button 523. The operator can also adjust the range of image capturing in the depth direction of the subject eye 207 by adjusting the depth adjustment button 524 to move the lens 235-10. Specifically, an AOSLO image of a desired layer, such as a visual cell layer, a nerve fiber layer, or a pigment epithelial layer. When the operator confirms that an AOSLO image is clearly displayed on the AOSLO display unit 518 and presses the AOSLO record button 520, AOSLO data is stored in the storage unit. Thereafter, the measurement light 206-1 is blocked.

Next at step S108, the angles of the nonconfocal apertures are set.

The operator operates the angle adjustment unit 554, specifically, rotates an angle indicator or the like. In response to the operation, the electrically driven stages 723 and 733 are driven in response to a signal from the control PC 106 so that the nonconfocal apertures 722 and 732 come to apparent angles on a specified fundus conjugate plane. The details of the operation will be described with reference o FIGS. 9A to 9E.

Figure 9A:
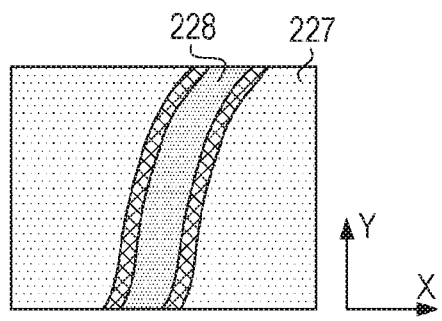
FIGS. 9A to 9E are diagrams illustrating an aperture disposition and an edge enhanced image according to the first embodiment.
Figure 9B:
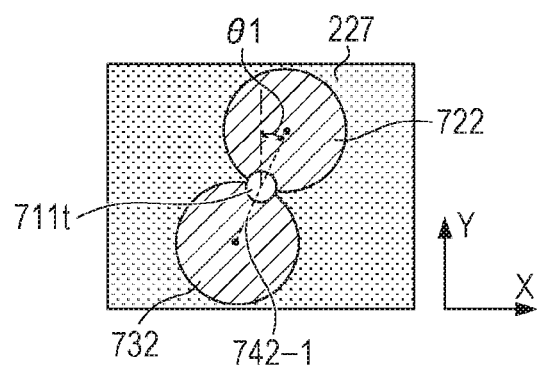
Figure 9C:
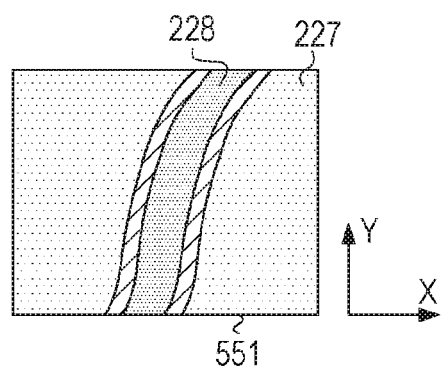
Figure 9D:
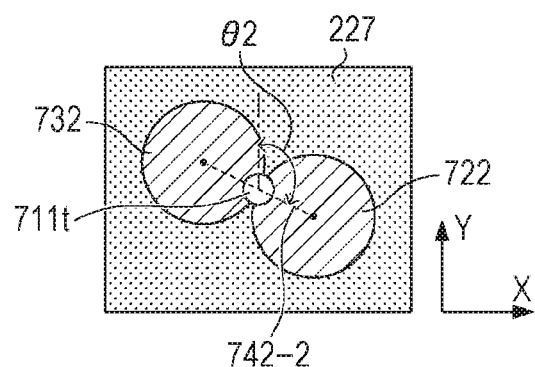
Figure 9E:
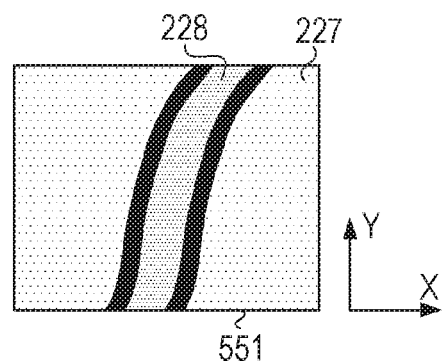

FIG. 9A is a confocal image of a blood vessel of the subject eye retina 227, in which a blood vessel 228 runs from the upper right to the lower left. As illustrated in FIG. 9B, if it is assumed that the apparent nonconfocal aperture disposition (θ1) on the fundus conjugate plane is set by the angle adjustment unit 554 from the upper right to the lower left substantially parallel to the running direction of the blood vessel 228, there is no large difference in intensity between diffused light passing through the aperture 722 and diffused light passing through the aperture 732. For this reason, an enhanced image generated from the difference between a signal from the detector 704-2 and a signal from the detector 704-3 is as illustrated in FIG. 9C, so that the edge of the blood vessel 228 cannot be enhanced. In contrast, if it is assumed that the apparent nonconfocal aperture disposition (θ2) on the fundus conjugate plane is set by the angle adjustment unit 554 from the upper left to the lower right substantially perpendicular to the running direction of the blood vessel 228, as illustrated in FIG. 9D, there is a large difference in intensity between diffused light passing through the aperture 722 and diffused light passing through the aperture 732. For this reason, an enhanced image generated from the difference between a signal from the detector 704-2 and a signal from the detector 704-3 is as illustrated in FIG. 9E, so that the edge of the blood vessel 228 can be enhanced. An indication indicating the set angles, for example, a straight line, may be displayed on the edge enhanced image displayed on the edge-enhanced-image display unit 551 at the center of the region or at a position designated by the operator.

Thus, by disposing the nonconfocal apertures in a direction suitable for the running direction of the linear structure of the subject, an edge enhanced image can be captured at the next step.

Next at step S109, an edge-enhanced AOSLO image is generated and displayed.

Here an edge enhanced image is generated by the control PC 106 using Eq. (1) for calculating an edge enhanced image on the basis of signals output from the detectors 704-2 and 704-3 obtained at the aperture disposition set at step S108. The edge enhanced image obtained by the calculation is displayed on the edge-enhanced-image display unit 551. Also at this step, the operator confirms that an edge enhanced image is clearly displayed on the edge-enhanced-image display unit 551. When the operator presses the AOSLO record button 520 after the confirmation, AOSLO data (the confocal image, the nonconfocal image, the edge enhanced image, and the set angles) is stored in the storage unit in association with subject-eye identification information.

Next at step S110, the operator determines whether to change the angles of the apertures. If yes, the process returns to step S106, and if no, the process proceeds to the next step.

Next at step S111, the operator determines whether to change the image capture position. If yes, the process returns to step S104, and if no, the process proceeds to the next step.

Next at step S112, the operator determines whether to switch the right and left eyes. If it is determined to switch the right and left eyes, the process returns to step S102, and if not, the process proceeds to the next step, where the STOP button 502 is pressed to end the image capturing processing.

Thus, in the present embodiment, the confocal light and nonconfocal light are spatially separated, and the nonconfocal light is split by amplitude by a beam splitter cube or the like, and an aperture is disposed in each optical path, and the apertures can be independently moved. With such a configuration, an enhance image can be generated at any angle with a simple configuration in which two apertures are independently moved. Furthermore, since two nonconfocal images are captured at the same time, from which an enhanced image is generated, an enhanced image coping with motion artifacts can be captured. This allows providing a high value image for diagnosis.

Second Embodiment

In the first embodiment, the apparent interval between the two apertures 722 and 732 on the fundus conjugate plane is only a predetermined interval. However, the present embodiment is characterized in that the apparent interval between the two apertures 722 and 732 is variable. Here, only the characteristics of the present embodiment will be described, and descriptions of the same configurations as the configurations of the first embodiment will be omitted.

Since the configuration of the AOSLO apparatus, the configuration of the control unit, the configuration of the optical system, and the configuration of the control software screen of the present embodiment are the same as the configurations of the first embodiment, descriptions thereof will be omitted. A characteristic processing procedure of image capturing in the present embodiment will be described with reference to FIG. 10 and FIGS. 11A to 11C.

Figure 10:
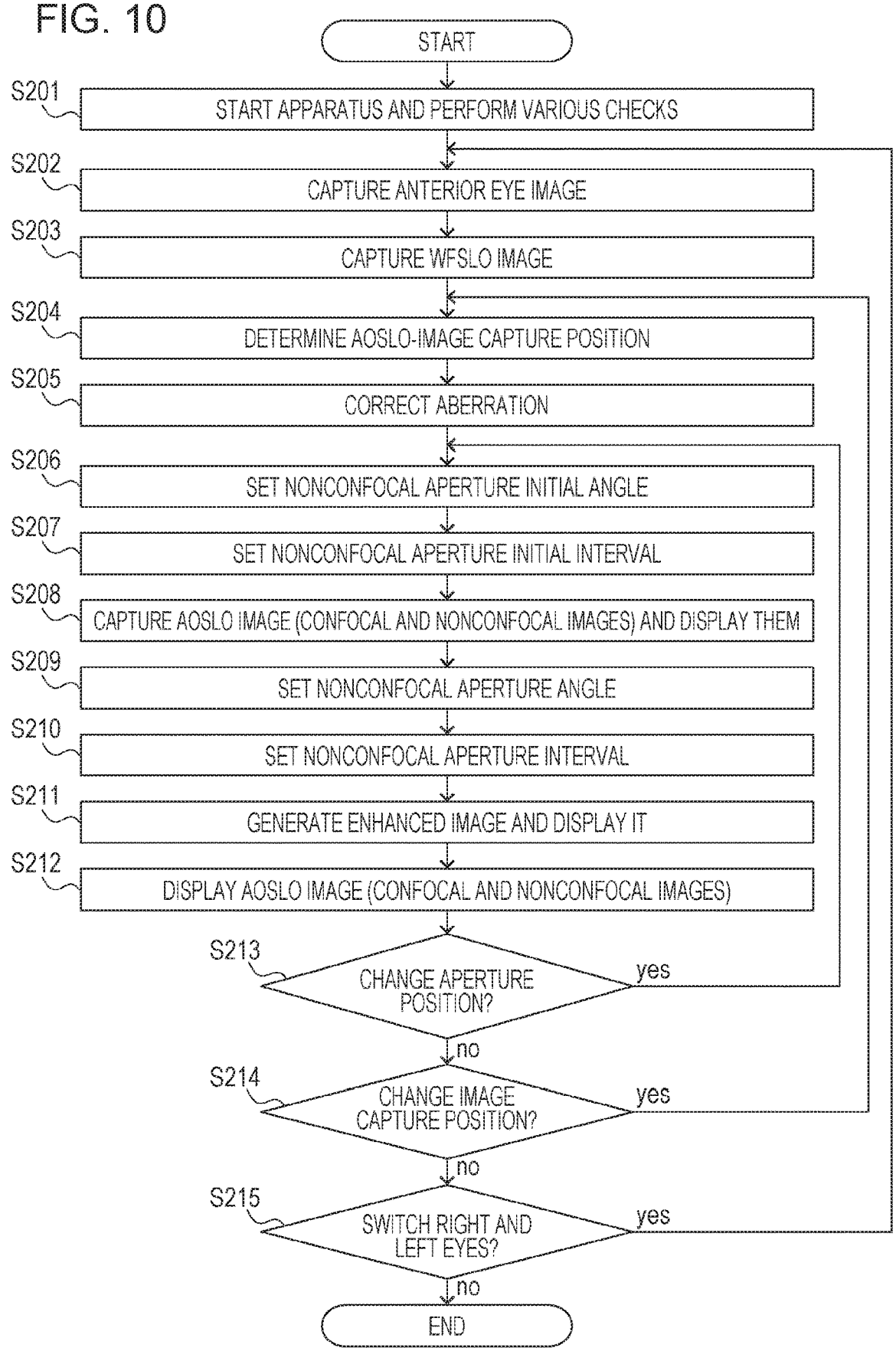
FIG. 10 is a flowchart for capturing processing according to a second embodiment of the present invention.

FIG. 10 illustrates the processing procedure of image capturing in the present embodiment. The process from step S201 to step S206 is the same as the process from step S101 to step S106 in the first embodiment, respectively.

At step S207, an apparent initial interval between nonconfocal apertures on a fundus conjugate plane is set. The initial interval is stored in advance in a memory (not illustrated) built in the control PC 106. An example is an initial interval at which the nonconfocal apertures are adjacent to each other. This is a mere example. An interval at the end of the previous examination may be used. After this step, the process goes to step S208, at which an AOSLO image is captured and displayed.

Step S208 and step S209 are the same as step S107 and step S108 of the processing procedure in the first embodiment.

Step S210 is a characteristic step in the present embodiment, at which the interval between the nonconfocal apertures is set.

The operator operates the aperture-interval adjustment unit 555, which is control software in FIG. 7, specifically, slides an interval indicator or the like. Then, the electrically driven stages 723 and 733 are driven in response to signals from the control PC 106 so that the nonconfocal apertures 722 and 732 are disposed at the indicated apparent interval on the fundus conjugate plane. The operation to change the apparent interval between the nonconfocal apertures on the fundus conjugate plane will be described with reference to FIGS. 11A to 11C.

Figure 11A:
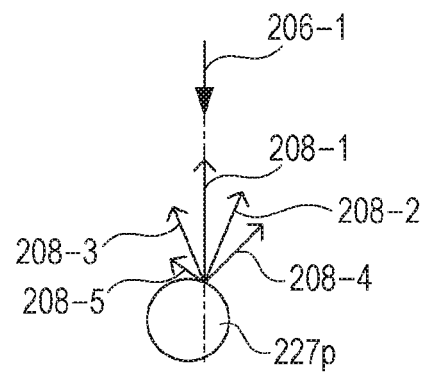
FIGS. 11A to 11C are diagrams illustrating an aperture disposition and an edge enhanced image according to the second embodiment.

FIG. 11A is a conceptual diagram illustrating a state in which the measurement light 206-1 applied to a structure 227p is reflected or diffused into the return light 208-1 to 208-5. In the distribution of the light reflected and diffused from the structure 227p, the return light 208-4 and 208-5 is at larger angles with respect to the optical axis of the measurement light 206-1 and has sufficiently smaller intensity than the intensity of the return light 208-2 and 208-3. Furthermore, the intensity of the return light 208-5 is sufficiently smaller than the intensity of the return light 208-4.

Figure 11B:
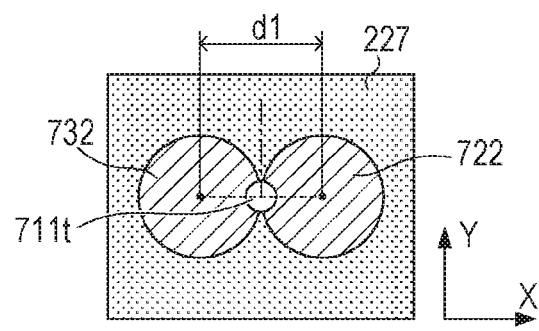
Figure 11C:
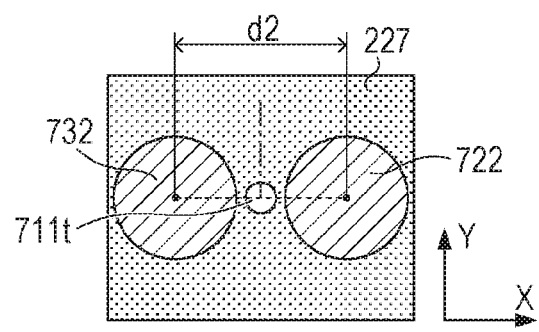

FIGS. 11B and 11C illustrate the apparent nonconfocal apertures 722 and 732 on the fundus conjugate plane and the transmission region 711t of the splitting unit 711. FIG. 11B illustrates a case in which the intervals between the nonconfocal apertures 722 and 732 is set small by an operation on the aperture-interval adjustment unit 555 at step S210, and FIG. 11C illustrates a case in which the interval is set large.

In the aperture disposition in FIG. 11B, the apparent interval between the nonconfocal apertures 722 and 732 on the fundus conjugate plane is d1. The return light 208-1, which is substantially coaxial with the measurement light 206-1 in FIG. 11A, enters the detector 704-1 through the transmission region 711t to generate a confocal image. The return light 208-2 and 208-4 leaning to +X with respect to the measurement light axis enters the detector 704-2 through the aperture 722 to generate a first nonconfocal image. The return light 208-3 and 208-5 leaning to −X enters the detector 704-3 through the aperture 732 to generate a second nonconfocal image. Since the proportion of the high-intensity return light 208-2 and 208-3 in the first and second nonconfocal images is large, the first and second nonconfocal images cannot sufficiently enhance the difference between the return light 208-4 and 208-5, so that high edge enhancement cannot be achieved.

In the aperture disposition in FIG. 11C, the apparent interval between the nonconfocal apertures on the fundus conjugate plane is d2 (d1<d2). The return light 208-1 in FIG. 11A enters the detector 704-1 through the transmission region 711t to generate a confocal image, as in FIG. 11B. The return light 208-4 enters the detector 704-2 through the aperture 722 to generate a first nonconfocal image. The return light 208-5 enters the detector 704-3 through the aperture 732 to generate a second nonconfocal image. In the aperture disposition in FIG. 11C, since the interval between the nonconfocal apertures 722 and 732 is large, the return light 208-2 and 208-3 does not pass through the transmission region 711t and the openings of the apertures 722 and 732. For this reason, the return light 208-2 and 208-3 is not applied to either of the detectors 704-2 and 704-3, not contributing to image formation. With such a configuration, the return light 208-4 and 208-5 with a large difference in intensity depending on the direction of diffusion is dominant in generating a nonconfocal image. This allows high edge enhancement in an enhanced image generated from two nonconfocal images.

Thus, by changing the apparent interval between the nonconfocal apertures on the fundus conjugate plane, the degree of edge enhancement can be changed. However, since the intensity of the return light generally increases with a decreasing distance to the confocal region, the signal intensity increases, allowing capturing an image with low noise.

Although a method for changing the apparent interval between the nonconfocal apertures on the fundus conjugate plane by the operation of the operator has been described here, the invention is not limited thereto. The interval may be automatically determined by the control PC 106. As described above, the intensity of return light due to diffusion generally decreases with an increasing distance from the confocal region, and increases with a decreasing distance. For this reason, if the outputs of the detectors 704-2 and 704-3 monitored are a predetermined threshold or more, the interval between the nonconfocal apertures 722 and 732 is increased until the outputs reach approximately the threshold. This allows generating an edge enhanced image with high edge enhancement while achieving a low-noise nonconfocal image. If the outputs of the detectors 704-2 and 704-3 are equal to or lower than the predetermined threshold, the interval between the nonconfocal apertures 722 and 732 is decreased until the outputs reach approximately the threshold. This allows generating an edge enhanced image with low noise.

Thus, if the intensity of ambient diffused light is high, the apertures are disposed away from each other, and if the intensity of ambient diffused light is low, the apertures are disposed close to each other. This allows generating an edge enhanced image with low noise regardless of the distribution of the light reflected and diffused from the subject.

Thus, by making the apparent interval between the nonconfocal apertures at the fundus conjugate position variable, an image with an enhanced edge can be generated, allowing imaging a microstructure. This provides a high value image for diagnosis.

Other Embodiments

Although the above embodiments of the present invention are configured to move light shielding members having an opening and detectors that receive light transmitted through the openings, the present invention is not limited to the configuration. For example, the present invention may also be configured to move a light shielding member including a reflecting portion and a detector that receives light reflected by the reflecting portion.

Embodiments of the present invention can also be realized by a computer of a system or apparatus that reads out and executes computer executable instructions (e.g., one or more programs) recorded on a storage medium to perform the functions of one or more of the above-described embodiments and/or that includes one or more circuits (e.g., application specific integrated circuit (ASIC)) for performing the functions of one or more of the above-described embodiments.

The programs and a computer-readable storage medium storing the programs are included in the present invention.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. An ophthalmic imaging apparatus comprising:
   a first splitting unit configured to split return light from a subject irradiated with measurement light into first and second light beams;
   first and second light receiving units configured to receive the first and second light beams obtained by the first splitting unit through first and second apertures disposed in respective optical paths of the first and second light beams, respectively;
   a generation unit configured to generate an image in accordance with light reception signals from the first and second light receiving units; and
   a moving unit configured to move the first and second apertures in a plane perpendicular to an optical axis,
   wherein the moving unit moves the first and second apertures independently.

2. The ophthalmic imaging apparatus according to claim 1, further comprising:
   a second splitting unit configure to split the return light into at least two light beams,
   wherein the first splitting unit splits one of the light beams obtained by the second splitting unit.

3. The ophthalmic imaging apparatus according to claim 2,
   wherein the second splitting unit splits the return light into central light and peripheral light, and
   wherein the first splitting unit splits the peripheral light.

4. The ophthalmic imaging apparatus according to claim 2, wherein the second splitting unit splits the central light of the return light using reflection or transmission.

5. The ophthalmic imaging apparatus according to claim 1, wherein an angle formed by the first and second apertures is variable at a position conjugate to the subject.

6. The ophthalmic imaging apparatus according to claim 5, wherein an angle of a linear structure of the subject in the image generated by the generation unit is calculated, and
   wherein the angle formed by the first and second apertures at the position conjugate to the subject is set to an angle substantially perpendicular to the angle of the linear structure.

7. The ophthalmic imaging apparatus according to claim 5,
   wherein the subject comprises a fundus,
   wherein the ophthalmic imaging apparatus further comprises an indication unit configured to indicate a position at which the measurement light is applied to the fundus, and
   wherein the angle formed by the first and second apertures is determined in accordance with an output from the indication unit.

8. The ophthalmic imaging apparatus according to claim 1, wherein an interval between the first and second apertures is variable at a position conjugate to the subject.

9. The ophthalmic imaging apparatus according to claim 1, wherein an interval between the first and second apertures at a position conjugate to the subject is determined in accordance with outputs from the first and second light receiving units.

10. The ophthalmic imaging apparatus according to claim 1,
    wherein the first splitting unit comprises a beam splitter cube, and
    wherein the light incident on the first splitting unit is substantially parallel light.

11. The ophthalmic imaging apparatus according to claim 1, wherein the moving unit moves the first and second light receiving units together with the first and second apertures, respectively.

12. The ophthalmic imaging apparatus according to claim 11, wherein the moving unit moves the first and second apertures, with a positional relationship between the corresponding first and second light receiving units kept.

13. The ophthalmic imaging apparatus according to claim 1, wherein the first and second light receiving units each have a light reception area capable of receiving light beams passing through the first and second apertures when the first and second apertures are moved, respectively.

14. The ophthalmic imaging apparatus according to claim 1, further comprising:
    a wavefront measuring unit configured to measure a wavefront of the return light from the subject; and
    a correction unit disposed in an optical system that projects the measurement light to the subject and configured to correct the wavefront of the measurement light projected to the subject,
    wherein the correction unit is driven based on the wavefront measured by the wavefront measuring unit.

* * * * *